United States Patent
Meir et al.

(10) Patent No.: US 11,006,493 B1
(45) Date of Patent: May 11, 2021

(54) LIGHTING SYSTEMS FOR GENERAL ILLUMINATION AND DISINFECTION

(71) Applicant: JUGANU LTD., Rosh Haain (IL)

(72) Inventors: Noam Meir, Herzliya (IL); Eran Ben-Shmuel, Rosh Haain (IL); Ada Lotan, Rosh Haain (IL); Alexander Bilchinsky, Rosh Haain (IL); Eran Efrati, Rosh Haain (IL); Jonathan Stok, Rosh Haain (IL); Yossi Bechor, Rosh Haain (IL); Yoav Bar, Rosh Haain (IL)

(73) Assignee: JUGANU LTD., Rosh Haain (IL)

( * ) Notice: Subject to any disclaimer, the term of this patent is extended or adjusted under 35 U.S.C. 154(b) by 0 days.

(21) Appl. No.: 16/850,760

(22) Filed: Apr. 16, 2020

Related U.S. Application Data

(63) Continuation-in-part of application No. 16/750,031, filed on Jan. 23, 2020, now Pat. No. 10,925,134, which is a continuation of application No. 16/425,083, filed on May 29, 2019, now Pat. No. 10,582,586.

(60) Provisional application No. 62/811,551, filed on Feb. 28, 2019, provisional application No. 62/677,405, filed on May 29, 2018.

(51) Int. Cl.
| | |
|---|---|
| *H05B 45/20* | (2020.01) |
| *G02B 6/00* | (2006.01) |
| *F21K 9/64* | (2016.01) |
| *F21V 8/00* | (2006.01) |
| *F21K 9/68* | (2016.01) |

(52) U.S. Cl.
CPC ............ *H05B 45/20* (2020.01); *F21K 9/64* (2016.08); *F21K 9/68* (2016.08); *G02B 6/0073* (2013.01)

(58) Field of Classification Search
CPC ........ H05B 45/00; H05B 45/20; H05B 45/22; H05B 47/155; G02B 6/0068; G02B 6/0073; G02B 6/005; G02B 6/0055; F21K 9/64; F21K 9/68; F21K 9/65; F21V 9/30; F21V 9/32; F21V 9/40; H01L 33/502; H01L 33/504; H01L 51/5036; F21Y 2113/10; F21Y 2115/10
See application file for complete search history.

(56) References Cited

U.S. PATENT DOCUMENTS

| | | | | |
|---|---|---|---|---|
| 8,174,189 | B2 * | 5/2012 | Kim | H01L 25/0753 313/512 |
| 8,858,836 | B2 * | 10/2014 | Duan | C09K 11/7737 252/301.6 P |
| 9,012,937 | B2 * | 4/2015 | Keller | H01L 33/504 257/98 |
| 9,101,036 | B2 * | 8/2015 | Guzan | D06P 1/0012 |
| 9,537,112 | B2 * | 1/2017 | Li | H01L 51/5036 |
| 9,560,714 | B1 * | 1/2017 | Hjerde | H05B 45/10 |
| 9,877,370 | B2 * | 1/2018 | Peeters | F21V 9/38 |
| 9,974,138 | B2 * | 5/2018 | Allen | F21V 23/04 |
| 10,582,586 | B2 * | 3/2020 | Meir | F21S 10/005 |

(Continued)

*Primary Examiner* — Haissa Philogene
(74) *Attorney, Agent, or Firm* — Morgan, Lewis & Bockius LLP

(57) ABSTRACT

Lighting systems combine UV-A and white light with an adjustable CCT value so that any adverse effects from the UV-A radiation are mitigated—that is, tunable adjustments to the output of the non-UV LEDs, or to all of the LEDs, result in an overall mixed output conforming to a target CCT value.

24 Claims, 17 Drawing Sheets

(56) References Cited

U.S. PATENT DOCUMENTS

2019/0093832 A1* 3/2019 Soer ...................... H01L 33/507
2020/0236760 A1* 7/2020 Meir ...................... H05B 45/20

* cited by examiner

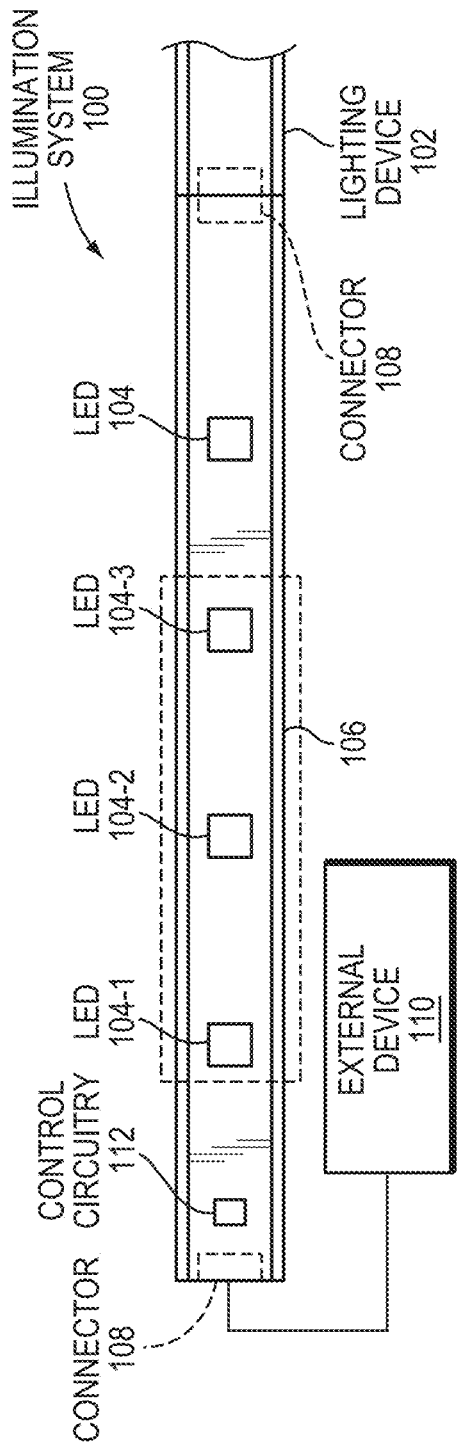
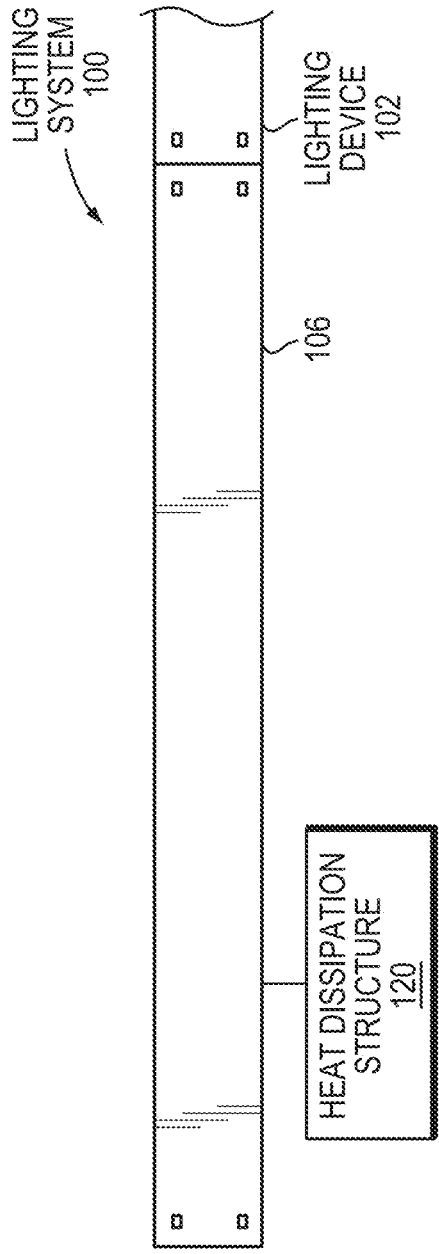
FIG. 1A
FIG. 1B

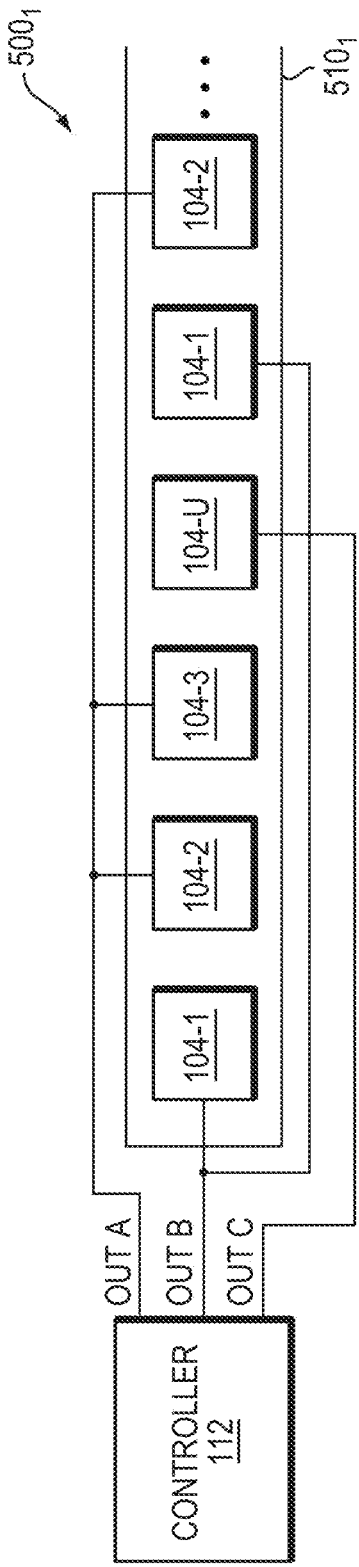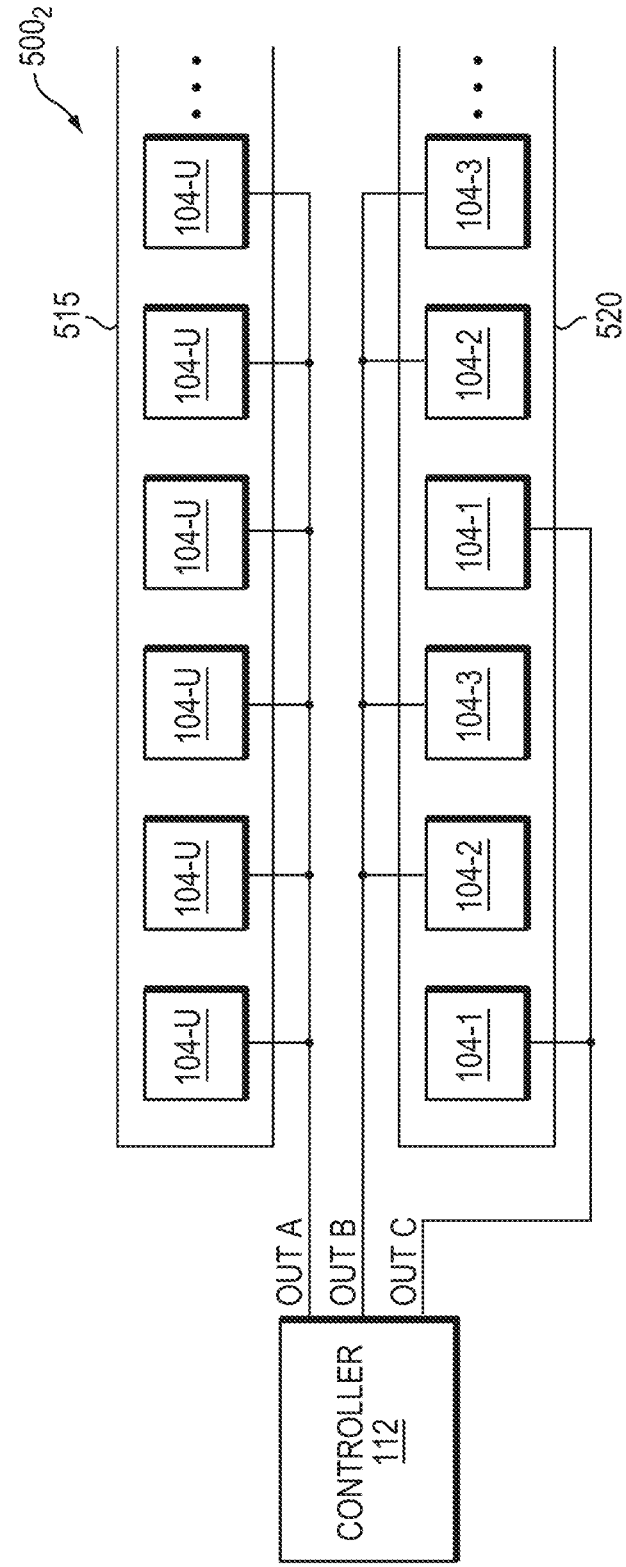

LIGHTING SYSTEMS FOR GENERAL ILLUMINATION AND DISINFECTION

CROSS-REFERENCE TO RELATED APPLICATION

This is a continuation-in-part of U.S. Ser. No. 16/750,031, filed on Jan. 23, 2020, which is itself a continuation of U.S. Ser. No. 16/425,083, filed on May 29, 2019, now U.S. Pat. No. 10,582,586, which claimed priority to U.S. Ser. Nos. 62/811,551 (filed Feb. 28, 2019) and 62/677,405 (filed May 29, 2018). The entire disclosures of all of the foregoing documents are hereby incorporated by reference.

TECHNICAL FIELD

The present invention relates generally to lighting systems, and in various embodiments to systems for providing mixed light for illumination and disinfection purposes.

BACKGROUND

It is known that certain wavelength ranges of light, particularly ultraviolet (UV) light, are germicidal—i.e., capable of killing or inactivating pathogens such as bacteria and viruses, rendering them incapable of causing disease. Illumination devices emitting germicidal light are frequently used to decontaminate medical tools and environmental surfaces. UV radiation is dangerous to humans, and some wavelength bands are more dangerous than others. As a result, broadband germicidal UV applications are typically deployed in oven-like devices that receive items to be decontaminated and are closed when the radiation is activated, thereby shielding personnel from harm. Although automated UV-based room-decontamination systems have been developed, these generally are not used when people are present. See, e.g., Livingston et al., "Efficacy of an ultraviolet-A lighting system for continuous decontamination of health care-associated pathogens on surfaces," *Am. J. Infection Control*, 48:337-339 (2020). Unfortunately, recontamination can occur quickly following device operation once people return and resume their activities.

The most effective germicidal wavelength band, UV-C (100-280 nm), is also the most dangerous to humans. The UV-A band (315-400 nm), on the other hand, can be safe for use in limited doses when people are present, and is known to have antimicrobial activity. Accordingly, it is possible to safely integrate UV-A lighting with general illumination, but the lighting sources used for these different wavelength ranges are different. Their outputs must be combined in a manner that preserves the quality of ambient light for affected personnel while ensuring safety.

SUMMARY

An increasing number of light fixtures utilize LEDs as light sources due to their lower energy consumption, smaller size, improved robustness, and longer operational lifetime relative to conventional filament-based light sources. Conventional LEDs emit light at a particular wavelength, ranging from, for example, red to UV light. However, for purposes of general illumination, the monochromatic emitted light by LEDs must be converted to broad-spectrum white light.

Embodiments of the present invention combine UV-A and white light with an adjustable CCT value so that any adverse effects from the the UV-A radiation are mitigated—that is, tunable adjustments to the output of the non-UV LEDs, or to all of the LEDs, result in an overall mixed output conforming to a target CCT value. In one embodiment, the LED illumination device employs an LED array having multiple LEDs that can be controlled individually or in a group to generate white light having a tunable CCT value within a range. Optionally, each of the LEDs may be disposed within a "cup-shaped" (e.g., parabolic) reflector for reducing "crosstalk" interactions between the light emitted from an LED and the photo-luminescent material(s) disposed above a neighboring LED. In addition, the reflector may be made of a high-reflectivity material so as to redirect upward light from the respective LED, thereby achieving at least partial collimation of the beam.

In various embodiments, the LEDs and/or photo-luminescent material(s) are encapsulated within a waveguide material made of, e.g., silicone. Light emitted from the LEDs, including unconverted light and light converted by the photo-luminescent material(s), can be mixed in a mixing region inside the waveguide and then directed to an output region for outputting white light for illumination. The illumination device may also include control circuitry for varying a parameter (e.g., the amplitude and/or duty cycle of the applied current or voltage) associated with each LED (or, in some embodiments, each group of the LEDs), thereby adjusting the CCT value of the mixed light to a target value.

Accordingly, in one aspect, the invention relates to a lighting device producing white light having a target CCT value and UV-A radiation. In various embodiments, the device comprises a plurality of red LEDs emitting red light having a wavelength between approximately 600 nm and approximately 670 nm, a plurality of blue LEDs emitting blue light having a wavelength between approximately 440 nm and approximately 485 nm, and a plurality of UV-A LEDs emitting UV radiation having a wavelength between approximately 315 nm and approximately 420; at least one photo-luminescent material for shifting a CCT value of at least one of (a) the red LEDs, (b) the blue LEDs or (c) the UV-A LEDs; and a waveguide material having (i) a mixing region for mixing the shifted and any unshifted light so as to generate white light having the target CCT value and (ii) an output region for outputting the white light. The red LEDs may have an emission peak at 630 nm, the blue LEDs have an emission peak at 450 nm, and the UV-A LEDs have an emission peak at 395 nm.

In some embodiments, the device also includes control circuitry for adjusting a parameter associated with at least one of the red LEDs, the blue LEDs or the UV-A LEDs so as to change the target CCT value of the generated white light. For example, the parameter may comprise at least one of an amplitude or a duty cycle of a current or a voltage associated with the red LEDs, the blue LEDs and/or the UV-A LEDs.

The control circuitry may be configured to adjust the parameter of each red LED, blue LED and UV-A LED to maintain the target CCT value while changing the intensity of the UV-A light. In some embodiments, the LEDs comprises a first group of the red LEDs and the UV-A LEDs electrically coupled to one another, a second group of the blue LEDs and the UV-A LEDs electrically coupled to one another, and a third group of the UV-A LEDs electrically coupled to one another; the control circuitry may be configured to adjust each of the groups individually. The UV-A LEDs in the third group may emit light at a wavelength having a lower interaction with the photo-luminescent material than the wavelengths emitted by the UV-A LEDs in the first group or the UV-A LEDs in the second group. Alternatively or in addition, the UV-A LEDs in the first group may emit light at a wavelength having a higher interaction with the photo-luminescent material than the UV-A LEDs in the second group. The photo-luminescent material may comprise at least one of a phosphor, a quantum dot material or a fluorescent dye.

In some embodiments, the lighting device further comprises a plurality of cup-shaped reflectors for at least partial collimation of light emitted from the LEDs, wherein each reflector has a top aperture and a bottom aperture and the bottom aperture has one of the LEDs disposed therein. At least one of the reflectors may be a parabolic reflector, and the respective LED disposed therein may be located at or near the focus of the parabolic reflector. The reflectors may comprise or consist essentially of silicone.

The lighting device may include an encapsulant material filled in a cavity space above one of the plurality of LEDs and surrounded by the respective reflector. In some embodiments, the lighting device further comprises a circuit board for mounting the LEDs thereon, and if desired, the lighting device may include a heat-dissipation structure thermally coupled to the circuit board for dissipating heat generated by the plurality of LEDs. In some embodiments, the lighting device further comprises at least one reflector located in the mixing region of the waveguide for promoting mixing of light. The waveguide material may comprise or consist essentially of silicone. The waveguide material may encapsulate at least one LED.

In another aspect, the invention relates to a lighting system comprising, in various embodiments, the lighting system includes a plurality of devices for producing white light having a target CCT value and UV-A radiation. Each of the devices may comprise a plurality of LEDs emitting visible light and a plurality of UV-A LEDs emitting UV radiation having a wavelength between approximately 315 nm and approximately 420; at least one photo-luminescent material for shifting a CCT value of at least some of the LEDs; a waveguide material having (i) a mixing region for mixing the shifted and any unshifted light and (ii) an output region for outputting the light; and a controller configured to operate the plurality of devices in (a) a normal mode, powering the LEDs, so as to generate white light having the target CCT value while emitting UV-A light or (b) in a boost mode, powering fewer than all of the LEDs emitting visible light and powering at least a majority of the UV-A LEDs at high intensity. In the normal mode, the UV-A light may have an intensity that is safe for human exposure and in the boost boost mode the intensity may exceed the intensity that is safe for human exposure. In the the boost mode, LEDs emitting red light may be operated to indicate a risk of harmful radiation. The plurality of LEDs emitting visible light may comprise (i) a plurality of red LEDs emitting red light having a wavelength between approximately 600 nm and approximately 670 nm and (ii) a plurality of blue LEDs emitting blue light having a wavelength between approximately 440 nm and approximately 485 nm.

The term "color" is used herein to denote the monochromatic or peak wavelength (or wavelengths) of light emitted by one or more LEDs. In addition, the term "uniform," as used herein, refers to a light intensity distribution whose lower and upper intensity limits are within a factor of four, preferably within a factor of two of each other. As used herein, the terms "approximately," "roughly," and "substantially" mean±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which:

FIGS. 1A and 1B depict a top view and a bottom view, respectively, of an example illumination system in accordance with various embodiments;

FIG. 5A depicts an exemplary LED configuration including groups of red, blue, and UV-A LEDs combined in series.

FIG. 5B depicts an exemplary LED configuration including groups of red and blue LEDs in one series and an adjacent series of UV-A LEDs.

DETAILED DESCRIPTION

Figure 1C:
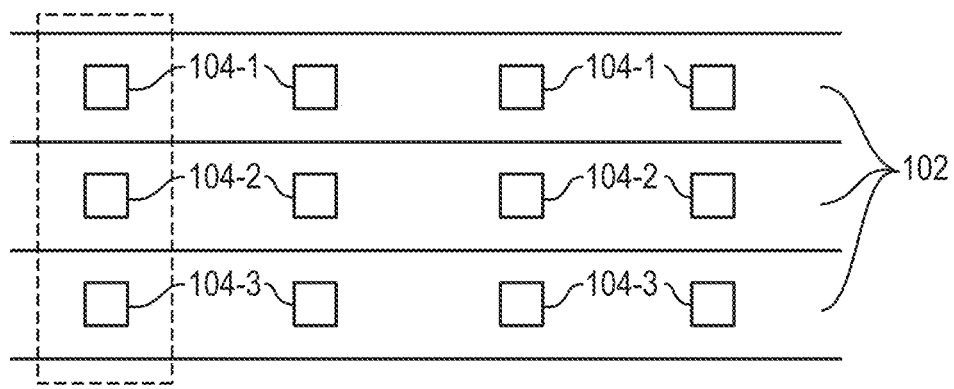
FIGS. 1C and 1D depict exemplary configurations of the LEDs in an illumination system in accordance with various embodiments.

FIG. 1A conceptually illustrates an exemplary illumination system 100 including one or more strip lighting devices 102 in accordance herewith; each strip 102 has an array of multiple LEDs 104 mounted to a circuit board 106 (e.g., printed circuit board, PCB). Each of the LED groups 104 may include one or more LED dies for emitting light with the same or different characteristics (e.g., colors, powers and/or CCT values). The LEDs 104 may be electrically coupled, via the circuit board 106, to connectors 108 mounted on each end of the circuit board 106. The connectors 108 may then electrically couple the LEDs 104 to an external device 110 (e.g., another lighting device, a dimming device, a power supply, an "Internet of things" (IoT) device, or a combination thereof) such that the LEDs 104 may receive power from the external device 110 via the connectors 108 and emit light.

In some embodiments, the LEDs 104 are electrically coupled to control circuitry 112 in the strip lighting device(s) 102. The control circuitry 112 may be configured to control operation of the LEDs 104 (e.g., by regulating the amplitude and/or duty cycle of the current and/or voltage applied to the LEDs 104), thereby regulating a characteristic (e.g., intensity or brightness) of the light emitted from the LEDs 104. For example, the control circuitry 112 may adjust the brightness of individual LEDs using pulse width modulation (PWM). For example, the control circuitry 112 may rapidly turn individual LEDs on and off at a high frequency that is imperceptible to humans. In this example, the brightness of the individual LEDs 104 may be changed by adjusting the ratio of on-time to off-time within a particular cycle (sometimes referred to as a "duty cycle"). The higher the ratio of on-time to off-time, the brighter the LED. Conversely, lowering the ratio of on-time to off-time dims the LED. Thus, the duty cycle may positively correlate to the average flux of the LED being controlled. The control circuitry 112 may vary the ratio of on-time to off-time based on control signals received from the external device 110 via the connectors 108. In one embodiment, the control circuitry 112 is implemented in circuitry that is external to the illumination system 100. For example, circuitry in the external device 100 may be configured to regulate the current and/or voltage applied to the LEDs 104, thereby directly controlling operations thereof. In this case, the control circuitry 112 may be omitted from the illumination system 100 altogether.

Generally, the LEDs 104, control circuitry 112, and/or the connectors 108 are all mounted to the circuit board 106. For example, the circuit board 106 may include one or more conductors to electrically couple the components mounted thereto. In addition, the circuit board 106 may be flexible to enable the illumination system 100 to conform to uneven surfaces. Referring to FIG. 1B, in some embodiments, the bottom surface of the circuit board 106 is connected to a heat dissipation structure 120 (e.g., a conventional heat sink) for dissipating heat generated by the LEDs 104.

The strip lighting device(s) 102 in the illumination system 100 may have particular dimensions to enable a wide range of applications. For example, the lighting devices 102 may have a depth of no more than approximately 1 inch, a length of no more than approximately 25 inches, and a width of no more than approximately 4 inches. It should be appreciated that the strip lighting devices 102 may be constructed with other dimensions, and may be two-dimensional arrays of LED groups rather than one-dimensional strips.

In various embodiments, the LEDs 104 are separated by a distance (e.g., 25 millimeters (mm) or 3 mm). In addition, each of the LEDs 104 may be configured to emit light with the same or different characteristic (e.g., wavelength, CCT value, etc.). In one embodiment, the strip lighting devices 102 include one or more groups of LEDs, each group including at least one red LED 104-1 having a wavelength between approximately 600 nm and approximately 670 nm, one "warm" white LED 104-2 emitting white light having a CCT value between approximately 1800K and approximately 2700K, and one "cool" white LED 104-3 emitting white light having a CCT value between approximately 3000K and approximately 6500K. The group of LEDs 104-1, 104-2, 104-3 may be aligned consecutively on the same strip lighting device 102 (as depicted in FIG. 1A) or in any suitable configurations for generating white light with an adjustable characteristic (e.g., a CCT value) as further described below. For example, referring to FIG. 1C, the group of LEDs 104-1, 104-2, 104-3 may be disposed on the same column on consecutive strips 102 abutting one another. Alternatively, referring to FIG. 1D, the two white LEDs 104-2, 104-3 may be disposed next to each other on the same strip 102 while the red LED 104-1 may be disposed next to one of the white LEDs 104-2, 104-3 but on a different strip.

The LEDs 104 may be operated individually or in a grouped manner. For example, each LED may be independently coupled to the control circuitry 112 such that the control circuitry 112 can separately control individual LEDs. Alternatively, some of the LEDs 104 may be wired together to allow the control circuitry 112 to control them as a single unit; different groups may or may not share one or more LEDs 104. For example, as described above, the illumination device 100 may include multiple groups of LEDs, each group including at least one red LED 104-1, one warm white LED 104-2, and one cool white LED 104-3. In one embodiment, the LEDs 104-1, 104-2, 104-3 in each group are electrically coupled such that the control circuitry 112 can control the LEDs 104-1, 104-2, 104-3 equivalently. In another embodiment, the red LEDs 104-1 in at least some groups are electrically coupled together; this allows the control circuitry 112 to control equivalently all red LEDs 104-1 that are electrically coupled. Similarly, the warm white LEDs 104-2 in at least some groups may be electrically coupled together, and the cool white LEDs 104-3 in at least some groups are electrically coupled together. This way, the groups of warm white LEDs 104-2 and cool white LEDs 104-3 may be separately controlled by the control circuitry 112 in a group manner.

Figure 2A:
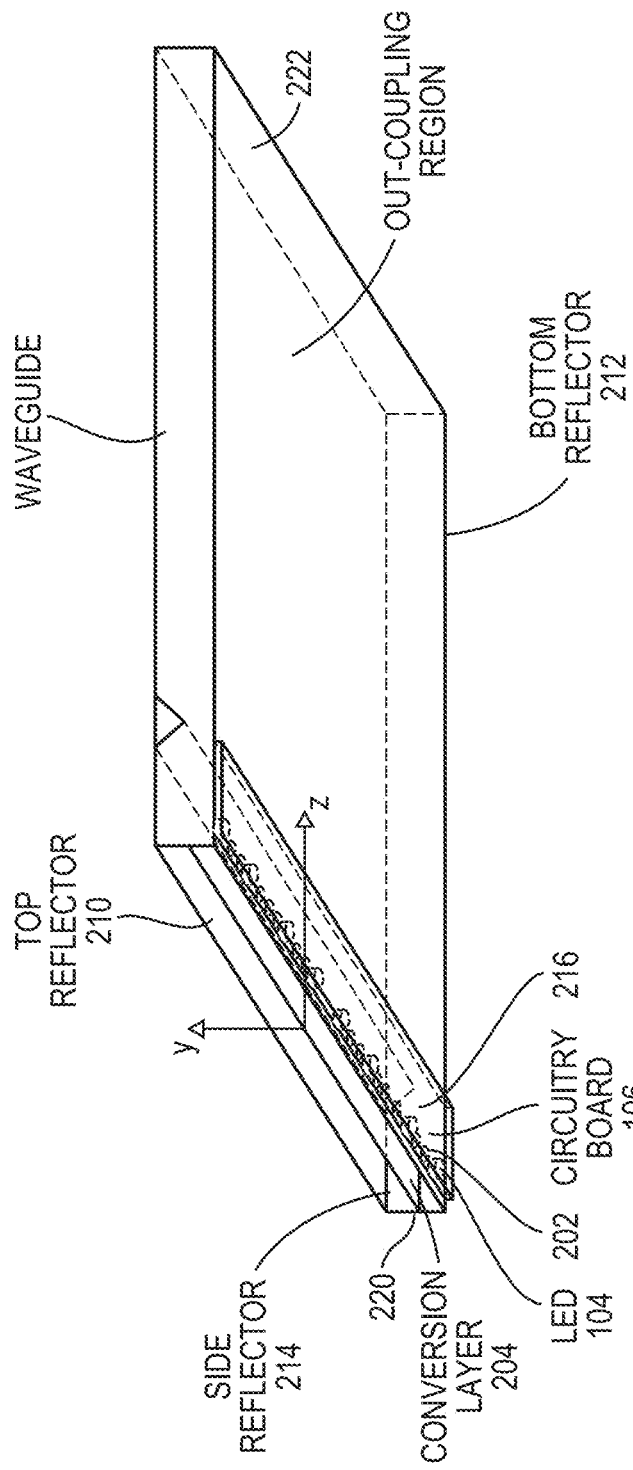
FIG. 2A schematically depicts an exemplary three-dimensional configuration of an illumination system in accordance with various embodiments.

Referring to FIG. 2A, in some embodiments, light emitted from the LEDs 104 travels through the space of a surrounding cavity 202 and is incident upon one or more conversion layers 204 that include one or more photo-luminescent materials (e.g., phosphors, quantum dot materials, etc.) for converting the LED light. The conversion layer(s) 204 absorbs at least some of the light emitted from the LEDs 104 and re-emits at least some of the absorbed light in a spectrum containing one or more wavelengths that are different from the absorbed light. In various embodiments, the photo-luminescent material(s) contained in the conversion layer(s) 204 is chosen based at least in part on the waveguide material. This is because the waveguide material may cause a larger portion of the blue light from the white LEDs 104-2, 104-3 to be extracted; this may result in a shift of the CCT value of light emitted from the white LEDs 104-2, 104-3 toward a higher CCT value (i.e., cooler white light). In one embodiment, the photo-luminescent material(s) on the conversion layer(s) 204 is chosen such that the wavelength shift thereby can at least partially counteract the shift resulting from the waveguide material as further described below. For example, the same or different photo-luminescent materials (e.g., phosphor QMK58/F-U2) may be applied to shift the CCT value of the light emitted from the cool white LED 104-3 toward a green CCT value and/or or to shift the CCT value of the light emitted from the warm white LED 104-2 toward a yellow CCT value.

Figure 2B:
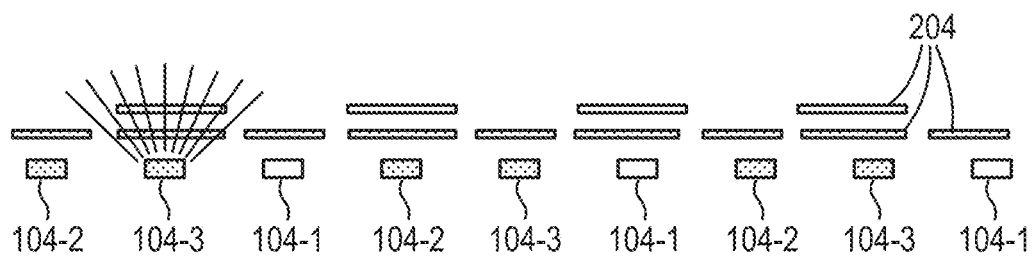
FIG. 2B depicts a spatial arrangement of LEDs and associated conversion layers for converting the wavelength of at least a portion of the LED light in accordance with various embodiments.

In one embodiment, the conversion layer(s) 204 is constructed from a foil that includes a composition of photo-luminescent materials. For example, the foil may be pre-made using a conventional substrate material (e.g., one or more layers of polymer such as PET) and a binder material (such as silicone); the composition of photo-luminescent materials is then disposed on the substrate surface. Referring to FIG. 2B, when multiple conversion layers 204 are used, the foils including different compositions of photo-luminescent materials may be placed on top of each other with or without a gap therebetween. In one embodiment, one or more layers made of polymer can be implemented to separate the conversion layers. In addition, a second layer made of the substrate material may be applied to the conversion layer(s) 204 so as to cover the photo-luminescent materials thereon. In some embodiments, the foil in the conversion layer(s) 204 includes one or more quantum dot materials. In addition, the foil may include a quantum dot enhancement film (QDEF) made by 3M Inc. or Nanoco Technology Ltd. to provide a geometry for deploying the quantum dot materials.

As described above, the conversion layer(s) 204 may absorb at least some of the light emitted from the LEDs 104 and re-emit (or converts) at least some of the absorbed light in a spectrum containing one or more wavelengths that are different from (typically longer than) the light emitted by the LEDs 104. The wavelength of the converted light may depend on the composition ratio of the photo-luminescent materials, the characteristics associated with each photo-luminescent material, and the wavelength of the light emitted from LEDs 104. The LEDs may include a monochrome LED with a narrow band spectrum (e.g., a red LED having a wavelength between approximately 600 nm and approximately 670 nm, a blue LED having a wavelength between approximately 400 nm and approximately 530 nm, and/or an UV LED having a wavelength between approximately 100 nm and approximately 400 nm) and/or a phosphor-converted LED with a wider band spectrum (e.g., the warm white LED 104-2 and/or cool white LED 104-3). The converted and unconverted light may then be mixed in the waveguide material to generate light having a target characteristic (e.g., color and/or CCT value); the target characteristic may be tunable within a range as further described below.

Figure 1D:
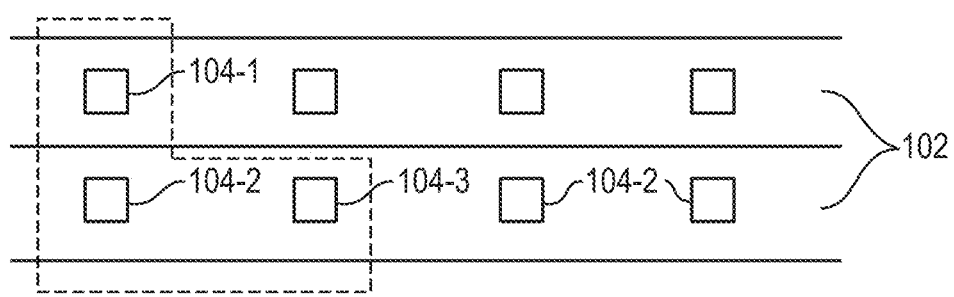
Figure 2C:
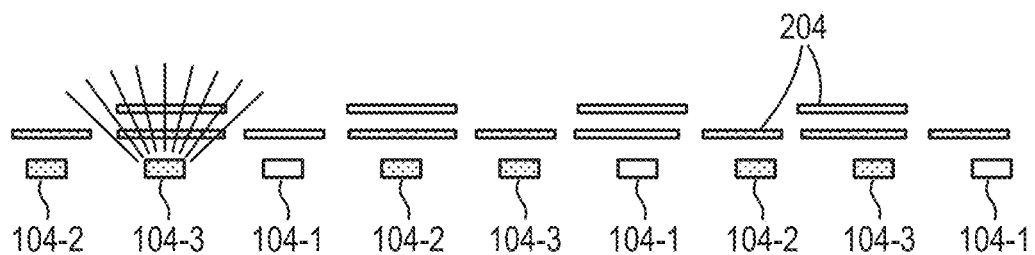
FIGS. 2C and 2D depict LED arrays including various combinations of different types of LEDs in accordance with various embodiments.

In some embodiments, each group of the LEDs depicted in FIGS. 1A, 1C and 1D may include one red LED 104-1 and two blue LEDs 104-2, 104-3 (instead of one red LED and two white LEDs described above). In addition, referring to FIG. 2C, the conversion layer(s) 204 may be disposed above the blue LEDs 104-2, 104-3 only, and not the red LED 104-1. The photo-luminescent material(s) may convert at least some of the blue light emitted from the blue LEDs 104-2, 104-3 to light having a longer wavelength. For example, a $(Gd, Y)_3(Al, Ga)_5O_{12}$ phosphor may convert blue light to yellow light. The converted light (e.g., yellow light) and unconverted blue light may then be mixed to generate white light. Thus, by choosing the photo-luminescent material(s) and/or adjusting the composition thereof, the light emitted from the blue LEDs 104-2, 104-3 may be converted to thereby generate warm white light and cool white light, respectively. In one embodiment, one or more additional conversion layers 204 are utilized to shift the CCT value of the light emitted from the cool white LED 104-3 toward a green CCT value and/or or to shift the CCT value of the light emitted from the warm white LED 104-2 toward a yellow CCT value as further described below.

Figure 2D:
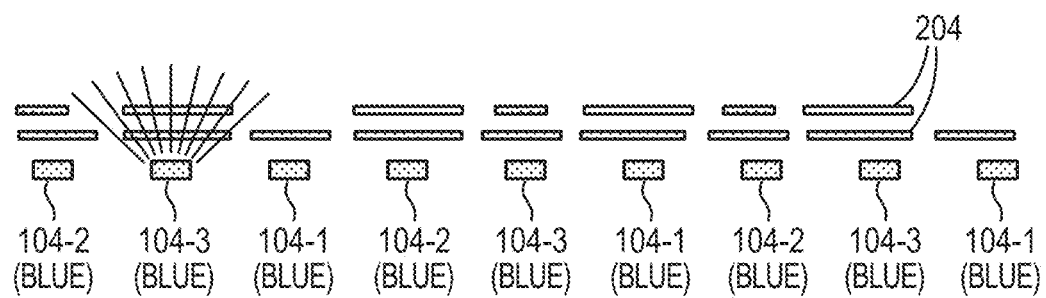

In some embodiments, the LED array includes blue LEDs only. For example, referring to FIG. 2D, light emitted from two of the blue LEDs 104-2, 104-3 may be converted to generate warm white light and cool white light as described above. In addition, the conversion layer(s) 204 having suitable photo-luminescent material(s) (e.g., deep-red quantum dots by Nanoco Technology Ltd.) may be disposed above the third blue LEDs 104-4 so as to convert the light emitted therefrom to red light having a peak wavelength at approximately 650 nm. Again, the light emitted from the LEDs, including both converted and unconverted light, may be mixed to generate light having a characteristic (e.g., color, CIE chromaticity coordinates and/or CCT value) that is tunable within a range.

Figure 2E:
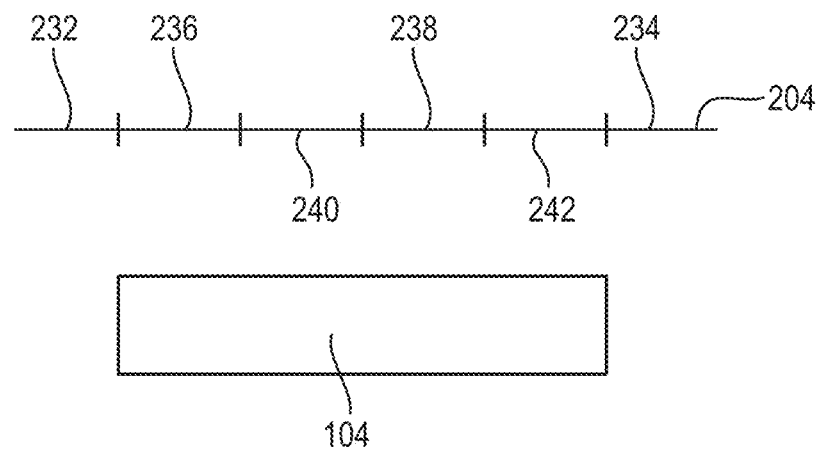
FIG. 2E depicts a conversion layer including multiple regions in accordance with various embodiments.

Referring to FIG. 2E, in various embodiments, the conversion layer(s) 204 is divided into multiple regions 232-242; each region is either uncoated or coated with the same or different photo-luminescent materials. For example, regions 232, 234 may be uncoated to allow unconverted blue light from the LED to travel through; regions 236, 238 may be coated with the first type of photo-luminescent material such that the converted light, after being mixed with the unconverted light, generates cool white light; and regions 240, 242 may be coated with the second type of photo-luminescent material such that the converted light, after being mixed with the unconverted light, generates cool white light. Thus, by utilizing different types of photo-luminescent materials having different characteristics at different locations over the LEDs 104, a target spectral power distribution (SPD) of the light may be achieved.

Figure 3A:
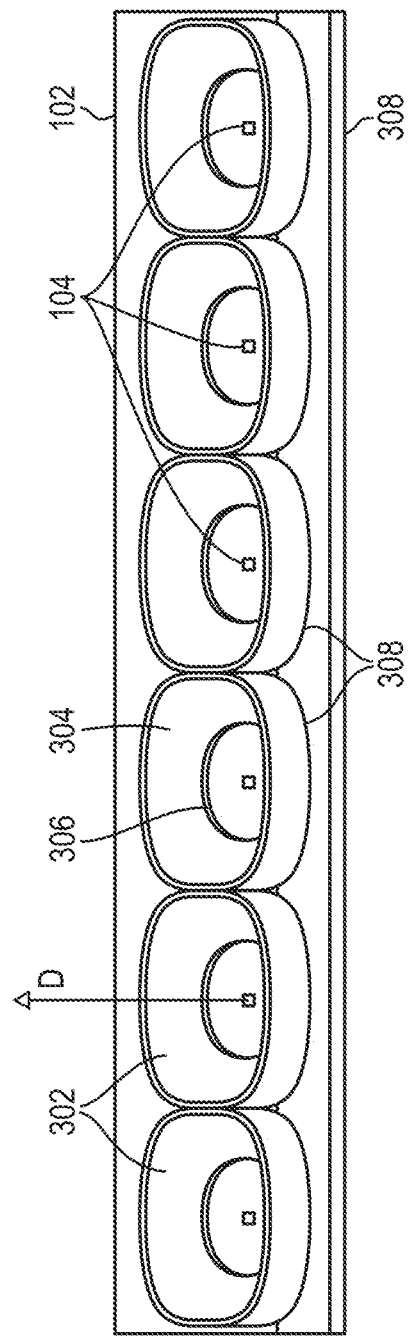
FIGS. 3A and 3B depict an implementation of reflectors surrounding the LEDs in an illumination system in accordance with various embodiments.

Referring again to FIG. 2B, the light emitted from an LED 104 may interact with the photo-luminescent material(s) disposed above a neighboring LED, cause a "crosstalk" interaction, and thereby result in additional colors. To reduce the crosstalk interaction, referring to FIG. 3A, each LED 104 in the strip lighting device 102 may be surrounded by a "cup-shaped" reflector 302. As shown, each cup-shaped reflector 302 typically has a top aperture 304 and a bottom aperture 306; the LED 104 is disposed inside of the bottom aperture 306. The shapes of the apertures 304, 306 may be, for example, circular, elliptical, rectangular, square, etc., and may be the same or different from each other. In one embodiment, the reflectors 302 abut each other such that the bottom portions 308 thereof form a continuous surface. The reflectors 302 may be made of a high reflectivity material, such as MS-2002 silicone from DOWSIL.

In some embodiments, the geometry of the cup-shaped reflectors 302 is configured to provide a uniform distribution of the light intensity at a specific distance, D, above the LED 104 where the conversion layer(s) 204 is typically disposed. In one embodiment, the reflector 302 is a parabolic reflector (i.e., a reflecting optic whose reflective surface forms a truncated paraboloid), and the LED 104 is placed at or near the focus of the paraboloid. Thus, a light beam emitted from the LED 104 onto the reflector 302 may be redirected upward for at least partial collimation of the beam.

Figure 3B:
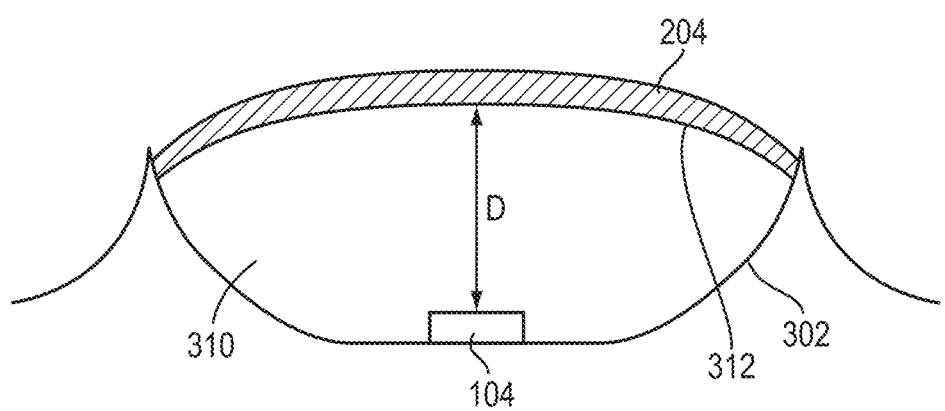

Referring to FIG. 3B, in various embodiments, an encapsulant material is potted over the LED 104 within a cavity space 310 created by the reflector 302 to at least partially encapsulate the LED 104. In one embodiment, the height of the encapsulant material above the LED 104 approximately corresponds to the specific distance D described above, thus the light intensity on the top surface 312 of the cavity space 310 may be uniformly distributed without having any visible high intensity spots thereon. The encapsulant material may include, consist of, or consist essentially of a clear material such as silicon. Alternatively, the encapsulant material may form a cover having a convex or domed shape on top of the reflector aperture 304; the cavity space 310 can be filled with gas or instead can be under vacuum. In addition, one or more conversion layers 204 including one or more types of photo-luminescent materials (e.g., phosphors, quantum dot materials, etc.) may be coated inside and/or outside the top surface 312 of the encapsulant material to convert the light emitted from the LEDs 104 as described above. In some embodiments, the cavity space 310 is at least partly filled by the encapsulant material that includes a composition of the photo-luminescent material(s) and waveguide material so as to allow the photo-luminescent material(s) to be embedded in the waveguide material.

Referring again to FIG. 2A, in one embodiment, the cavity 202 formed between the circuit board 106 and the conversion layer(s) 204 is filled with a waveguide material (e.g., silicone) such that the waveguide material is in direct contact with the top surface of the circuit board 106 and the conversion layer(s) 204. In addition, one or more reflectors 210-214 may be disposed on the top, bottom and/or side surfaces of the waveguide, respectively, such that the light emitted from the LEDs 104, including both unconverted and converted light by the conversion layer(s) 204, can be mixed inside a mixing region 216 of the waveguide; the mixed light then propagates to an output region 218 of the waveguide for outputting the light. In addition, a reflector 219 may be disposed on the top surface of the circuit board 106. In one embodiment, at least one of the reflectors 210-214, 219 is made of a high-reflectivity silicone (e.g., CI2001 from DOWSIL). Alternatively, a high-reflectivity foil may be used as one or more of the reflectors 210-214, 219. It should be noted that although FIG. 2A depicts the LEDs 104 and conversion layer(s) 206 disposed on one side 220 of the waveguide only, they may be disposed on another side 222 with the similar spatial arrangement. In addition, the location of the output region 218 may be anywhere on the waveguide and is not limited to the top surface of the waveguide as depicted in FIG. 2A.

In one implementation, the entire circuit board 106 is encapsulated inside the waveguide; the illumination system 100 may include a heat-conducting path connecting the bottom surface of the circuit board 106 to an outer surface of the waveguide for dissipating heat generating by the LEDs 104. In one embodiment, the heat-conducting path is formed by using a heat conductive material as a part of the waveguide material and disposing the circuit board 106 to be in directly contact with the waveguide.

Figure 4A:
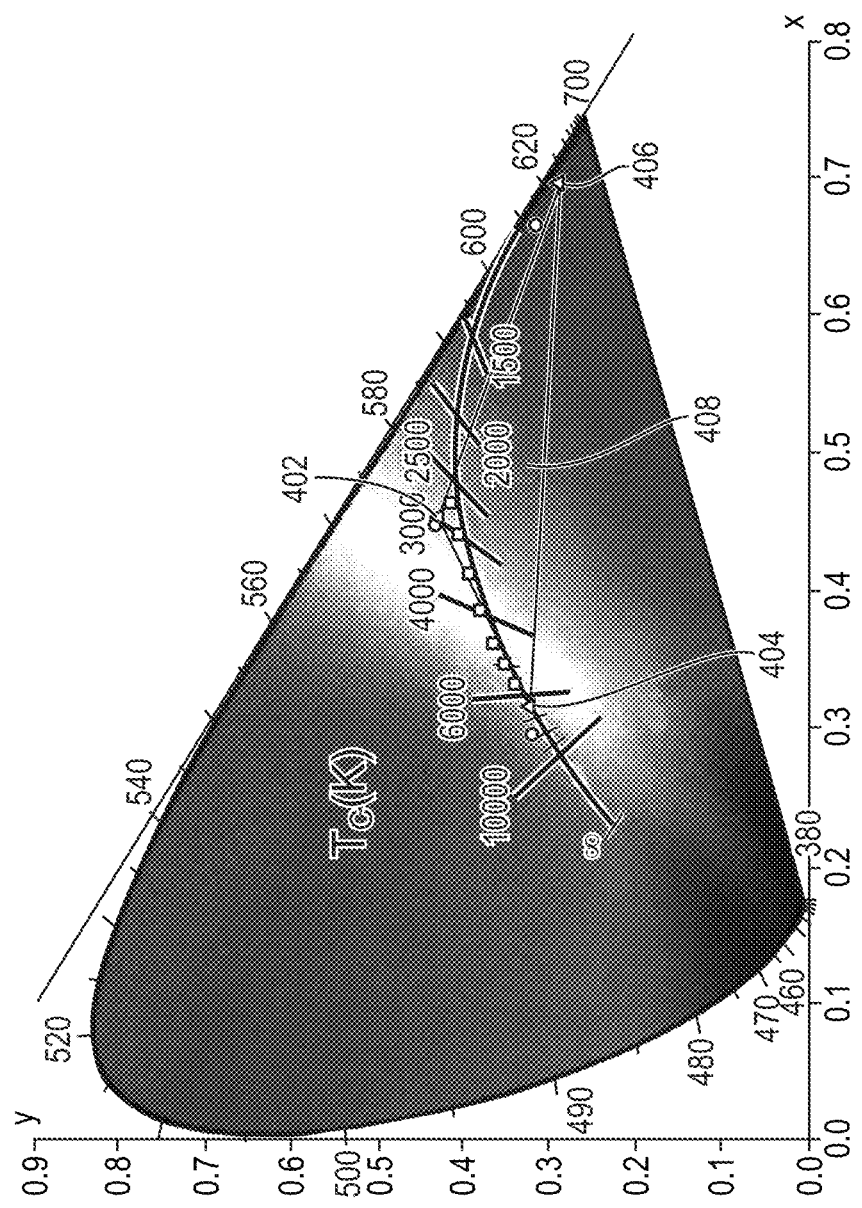
FIGS. 4A and 4B depict exemplary color coordinates of the light emitted from a warm white LED, a cool white LED, and a red LED in the CIE 1931 color space in accordance with various embodiments.
Figure 4B:
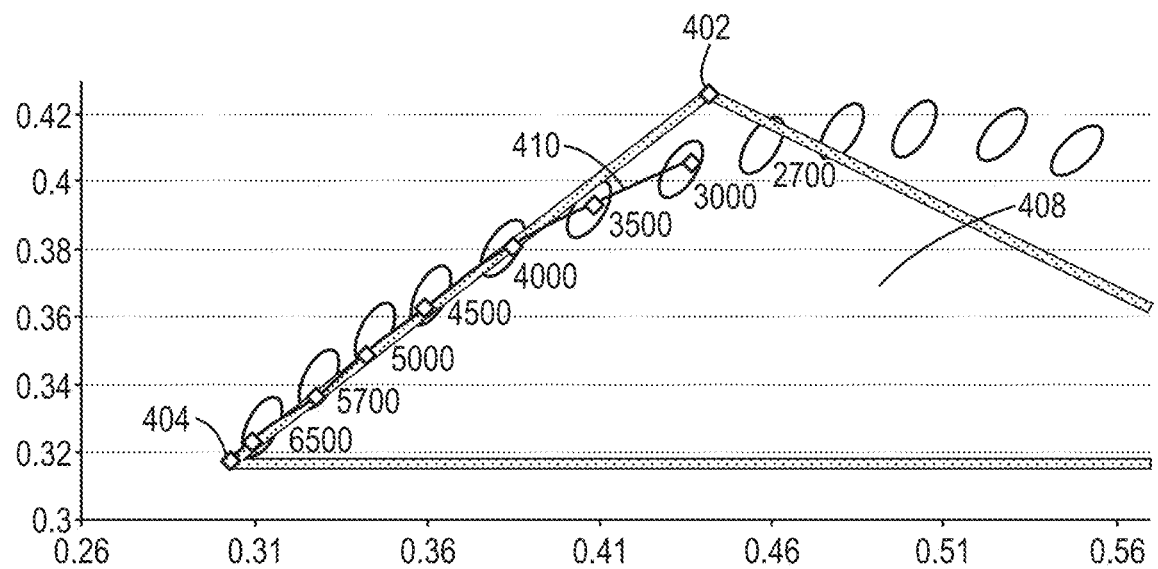

As discussed above, the LEDs 104 mounted on the circuit board 106 may be controlled individually or in a group manner to generate light having a tunable CCT value within a range. The particular range in which the CCT value can be varied may depend on the configurations of the LEDs, such as the particular combination of the LEDs. FIG. 4A depicts exemplary color coordinates 402, 404, 406 of the warm white LED 104-2, cool white LED 104-3, and red LED 104-1, respectively, in the CIE 1931 color space in accordance with various embodiments. As shown, the color coordinates 402, 404, 406 form vertices of a triangular region 408; thus, the color coordinates of light produced by such a combination of LEDs 104-1, 104-2, 104-3 can be tuned within the triangular region 408. FIG. 4B depicts an enlarged view of a region of the triangular region 408. As shown, the CCT value of the light generated by the red LED, warm white LED and cool white LED can be tuned along the Black Body Curve 410 with a deviation of less than 3.0 SDCM (MacAdam's ellipse). Further details about combining various LEDs to generate white light having a tunable CCT value are provided, for example, in International Application No. WO 2018/157166 (filed on Feb. 27, 2018), the entire content of which is incorporated herein by reference.

Figure 4C:
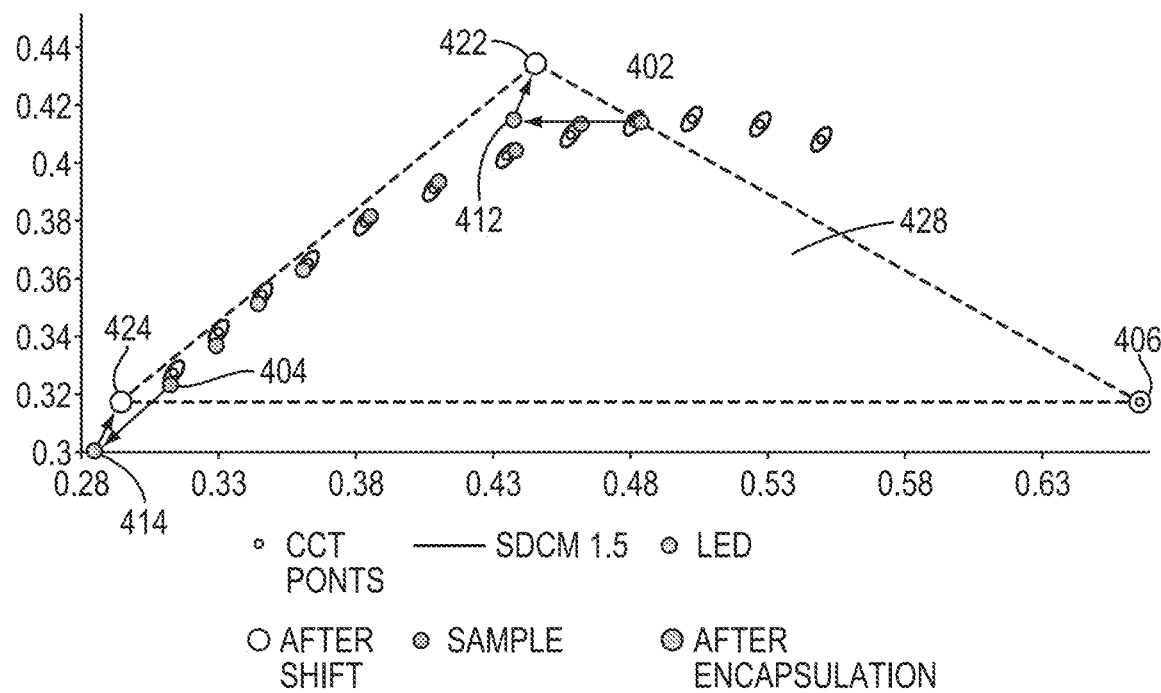
FIG. 4C depicts shifts of color coordinates in the color space resulting from a waveguide/encapsulant material and one or more photo-luminescent materials in accordance with various embodiments.

As described above, the LEDs 104 may be encapsulated in a waveguide material (FIG. 2A) and/or an encapsulant material (FIG. 3B). As a result, a large portion of the blue light from the LEDs is extracted from the LEDs, which in turn causes shifts of the CCT values associated with the warm white light and cool white light. For example, referring to FIG. 4C, the color coordinates of the light emitted from the warm white LED 104-2 may be shifted from a location 402 (approximately 2700K) to a location 412 (3000K); similarly, the color coordinates of the light emitted from the cool white LED 104-3 may be shifted from a location 404 (approximately 6500K) to a location 414 (8000K). The degree of shifting may depend on the material characteristics of the waveguide and/or an encapsulant. It should be noted that because the waveguide material and/or encapsulant material has no (or at least limited) effect on the color coordinates 406 of the red light emitted from the red LED 104-1, there may be no need for applying the photo-luminescent material(s) thereto.

In various embodiments, the color coordinate shifts resulting from the waveguide and/or encapsulant are at least partially counteracted by using, for example, one or more photo-luminescent materials (e.g., phosphor QMK58/F-U2) disposed on the conversion layer(s) 204. In one embodiment, the photo-luminescent material(s) shifts the CCT value of the light emitted from the cool white LED 104-3 toward a green CCT value (e.g., from the location 414 to a location 424) and/or the (Cx, Cy) value of the light emitted from the warm white LED 104-2 toward a yellow (Cx, Cy) value (e.g., from the location 412 to a location 422). As a result, the color coordinates of the light generated by mixing the cool white light, warm white light and red light that have color coordinates at locations 424, 422, 406, respectively, can be tuned within a new triangular region 428 formed by the new vertices 424, 422, 406. In various embodiments, the CCT value of the mixed light can be tuned along the Black Body Curve 410 with a deviation of less than 1.5 SDCM.

Figure 4D:
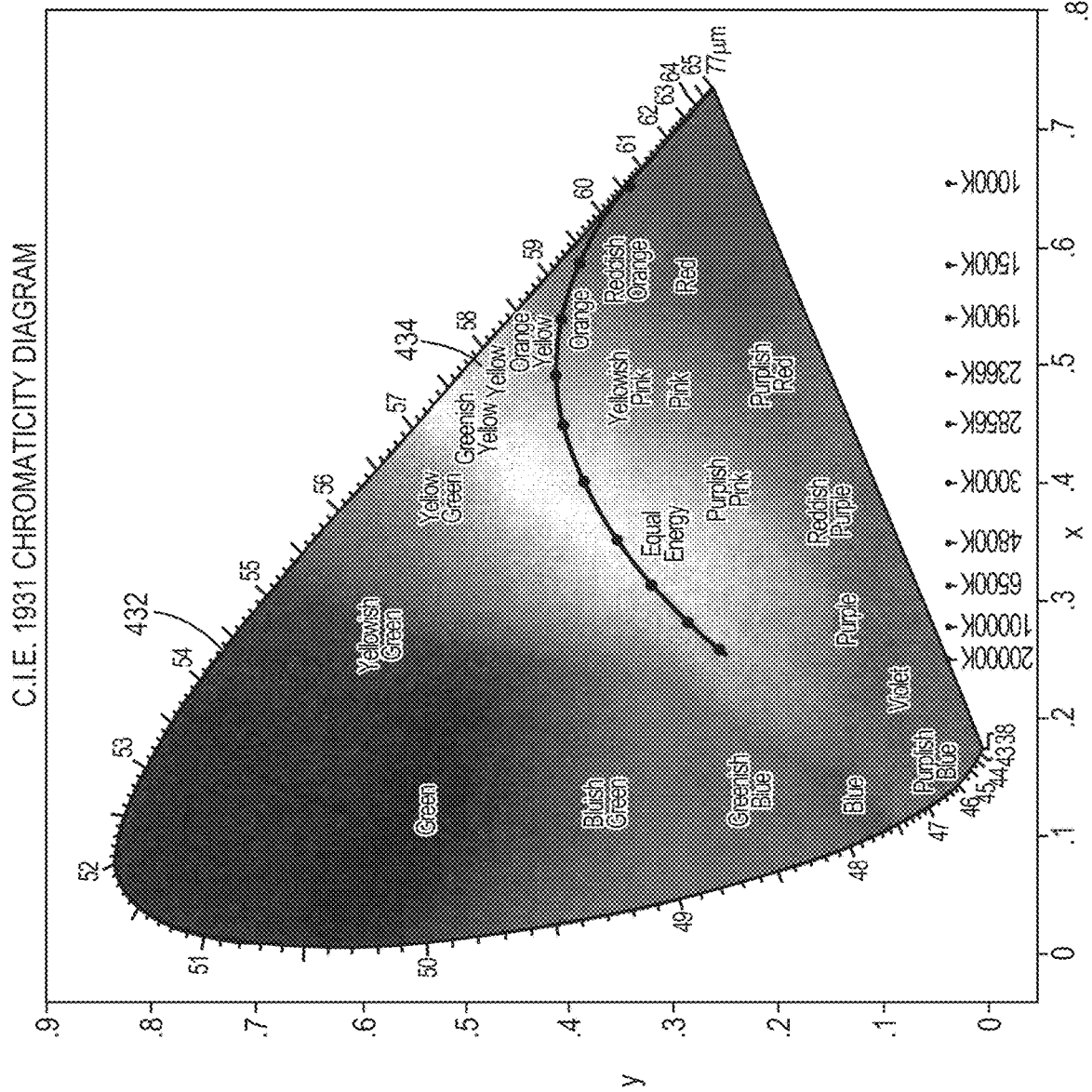
FIG. 4D depicts a green region and a yellow region in the CIE 1931 color space in accordance with various embodiments.

It should be noted that the green CCT value and yellow CCT value toward which the CCT values of the cool white light and warm white light are shifted do not necessarily correspond to specific CCT values. Rather, referring to FIG. 4D, the green CCT value and yellow CCT value can be any color coordinates located within the green region 432 and yellow region 434 in the color space. In addition, for purposes hereof, the green region 432 includes all color coordinates in the color space corresponding to wavelengths between approximately 480 nm and approximately 550 nm, and the yellow region 434 includes all color coordinates in the color space corresponding to wavelengths between approximately 550 nm and approximately 590 nm.

Figure 4E:
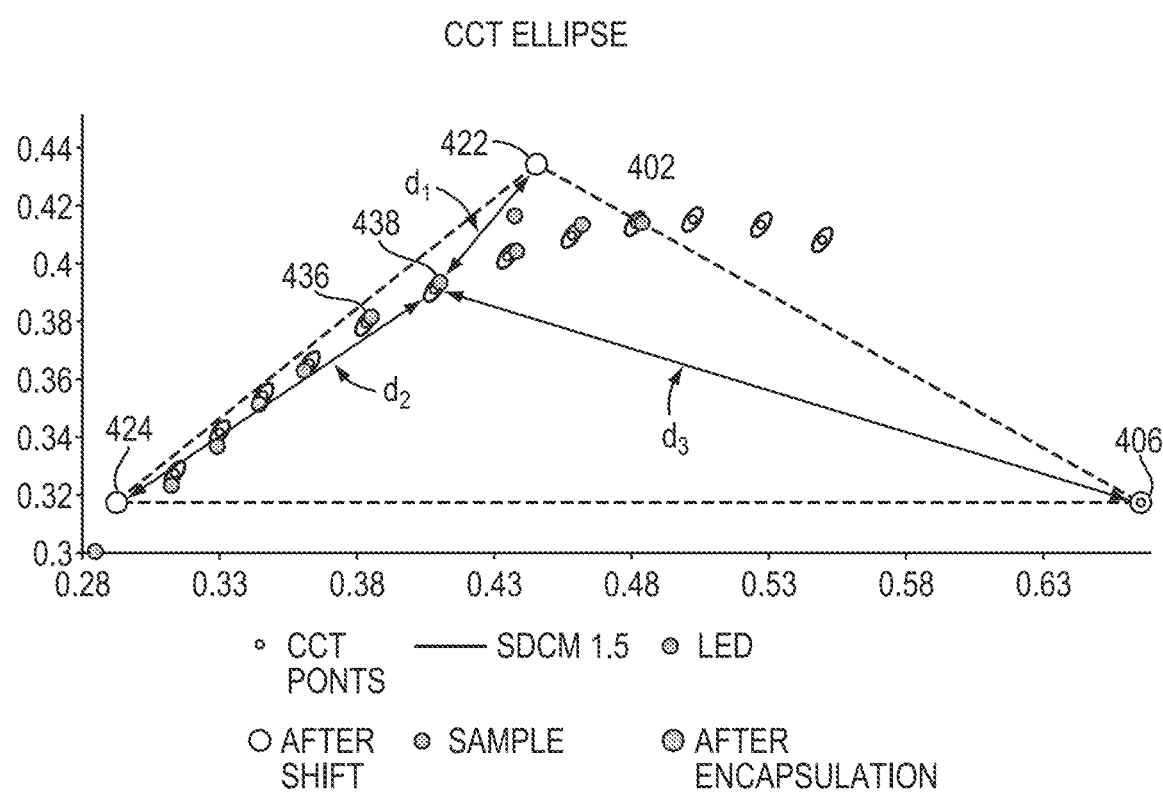
FIG. 4E depicts adjustments of the CCT value along the Black Body Curve (BBC) in accordance with various embodiments.
Figure 4G:
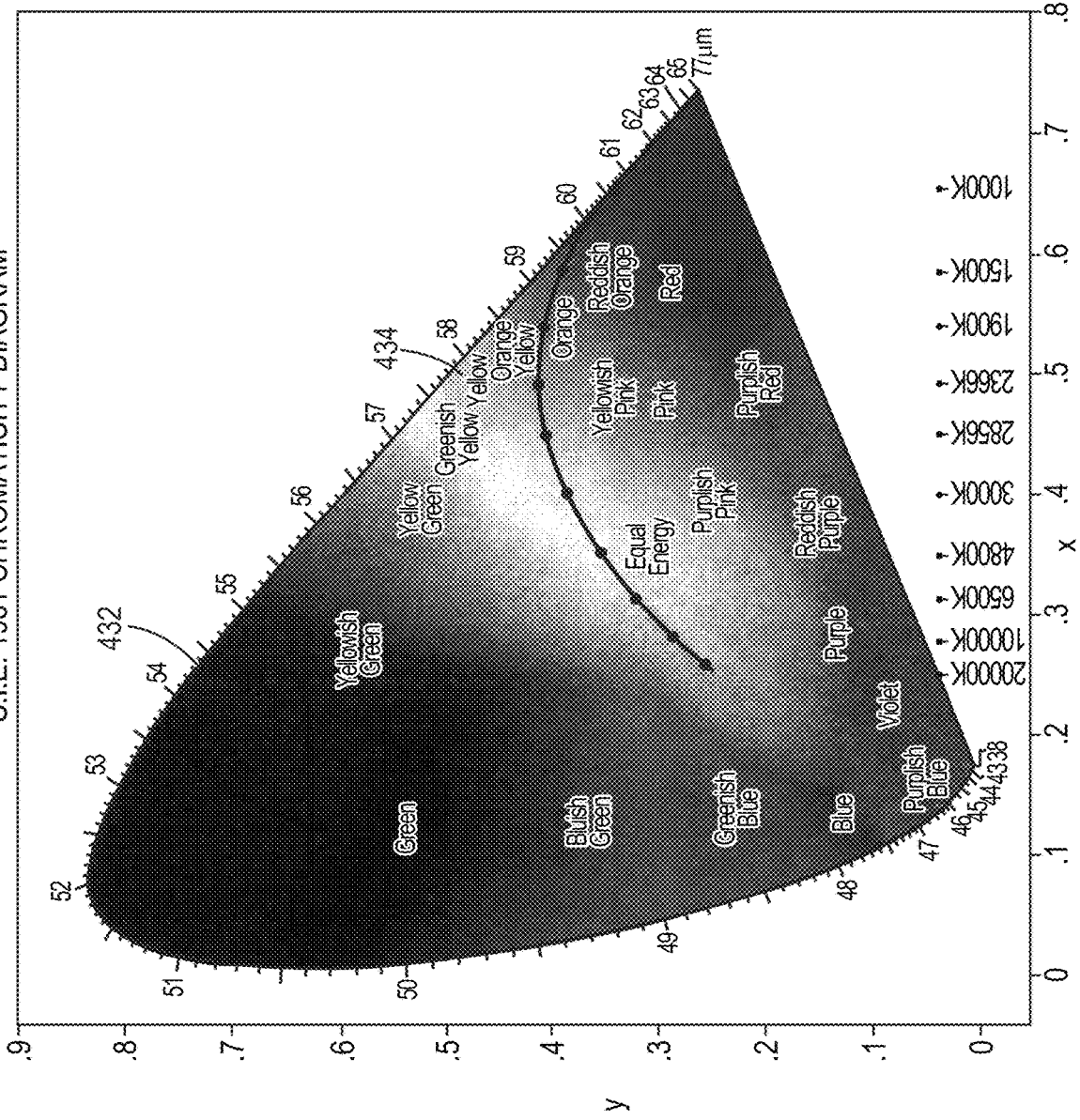

Referring to FIG. 4E, in various embodiments, the CCT value of the mixed light is adjusted along the BBC with a deviation of less than 1.5 SDCM so as to match or complement the human circadian rhythm. The adjustment of the CCT value can be achieved by changing the intensity of the light emitted from one or more of the LEDs 104-1, 104-2, 104-3. For example, when a target CCT value of the mixed light changes from a location 436 to a location 438 in the color space, the intensity of the cool white LED 104-3 may be reduced, while the intensity of the warm white LED 104-2 and/or red LED 104-1 may be increased. In various embodiments, the intensity contribution of the light from each LED negatively correlates to the distance between the color coordinates of the LED light and the target color coordinates in the color space. For example, assuming the target color coordinates being at the location 438, because the distance, $d_1$, between the color coordinates 422 of the warm white light and the target color coordinates 438 is smaller than the distance, $d_2$, between the color coordinates 424 of the cool white light and the target color coordinates 438, the intensity contribution from the warm white light may be larger than that from the cool white light. Similarly, because the distance $d_2$ is smaller than the distance, $d_3$, between the color coordinates 406 of the red light and the target color coordinates 438, the intensity contribution from the cool white light may be larger than that from the red light.

In some embodiments, the control circuitry 112 adjusts the intensity of the light emitted from one or more of the LEDs 104-1, 104-2, 104-3 by varying the amplitude and/or duty cycle of the current and/or voltage associated therewith. In addition, the control circuitry 112 may include a look-up table that maps particular target CCT values to a set of intensity ratios for the LEDs within the LED array. Thus, when the control circuitry 112 receives information indicative of a desired CCT value, it may access the look-up table to retrieve the corresponding intensity ratios, and, based thereon, adjust the intensities of the LEDs.

Figure 5C:
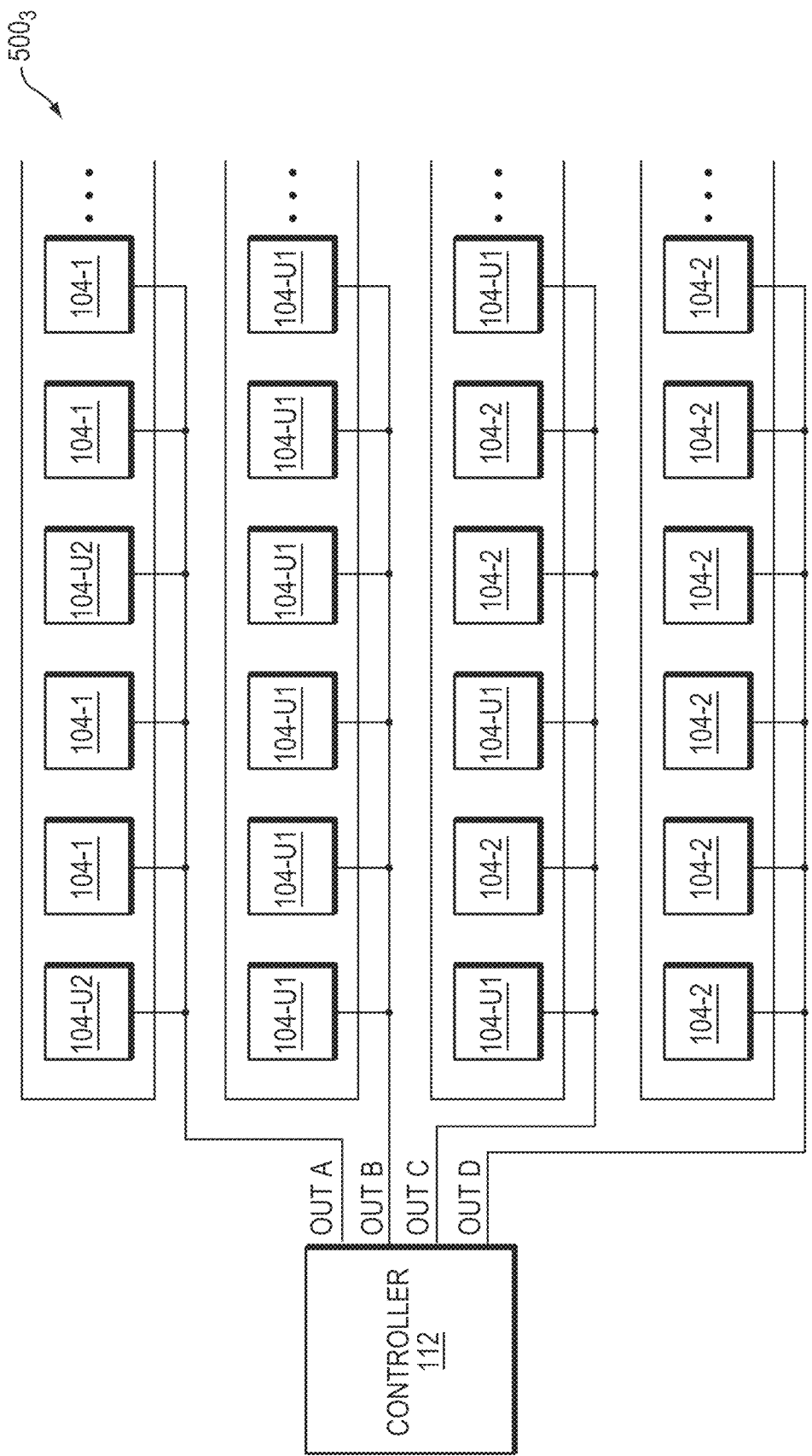
FIG. 5C depicts an exemplary LED configuration including red and blue LEDs and two types of UV-A LEDs.

Refer now to FIGS. 5A-5C, which illustrate representative configurations $500_1$, $500_2$ for combining germicidal UV-A light with light in the visible range to create white light with a desired CCT value. Although the term UV-A commonly refers to the wavelength region 315-400 nm, for purposes of this specification UV-A refers to the broader wavelength region 315-420 nm. In the configuration $500_1$, LEDs 104-U emitting UV-A light are grouped with three other LEDs 104-1, 104-2, 104-3. These groups repeat in a linear sequence along a PCB $510_1$. In one embodiment, the LEDs 104-1 are red and the LEDs 104-2 and 104-3 are both blue (although they may be different LED types). In the configuration presented in FIG. 5C, two types of LED emitting UV-A light (e.g., at different wavelengths), 104-U1 and 104-U2, are connected in series together with LEDs 104-1—in the top row, LEDs 104-U1 are used and in the third row, LEDs 104-U2 are used. The alternate (second and fourth) rows consist entirely of a single UV or non-UV LED type. This configuration allows each row to be driven by a single channel and collectively produces white light through the phosphor while also providing UV-A light.

The illustrated linear sequence is only one example of groupings, however; in other implementations, the groupings are spread across linear LED sequences as shown in FIGS. 1C and 1D.

Suitable LEDs are as follows:

| LED | 104-U1 LxF3-U390100007001 | 104-U2 LHUV-0405-A070 | 104-3 SB1515NS | 104-2 SB1515NS | 104-1 LXZ1-PD02 |
|---|---|---|---|---|---|
| Peak Wavelength [nm] | 395 | 405 | 450 | 450 | 630 |
| Radiant Power [mW] | 750 | 750 | 900 | 900 | 350 |
| Current [mA] | 500 | 500 | 500 | 500 | 500 |
| Forward Voltage [V] | 3.1 | 3.1 | 3 | 3 | 2.2 |
| Number of LEDs | 8 | 4 | 4 | 8 | 6 |

The controller 112 has three output channels A, B, C. Channel A controls the blue LEDs, channel B controls the red LEDs, and channel C controls the UV-A LEDs. Once again, the control circuitry 112 adjusts the intensity of the light emitted from one or more of the LEDs 104-1, 104-2, 104-3, 104-U by varying the amplitude and/or duty cycle of the current and/or voltage associated therewith. In some embodiments, only the amplitude and/or duty cycle of the visible-light LEDs 104-1, 104-2, 104-3 is controlled; in other embodiments, the amplitude and/or duty cycle of all LEDs is controlled.

In the configuration $500_2$ shown in FIG. 5B, the UV-A LEDs are deployed on a single printed circuit board (PCB) 515, and the LEDs 104-1, 104-2, 104-3 are deployed on an adjacent PCB 520. The lighting system may include a sequence of PCBs 515, 512, e.g., alternating or present in different quantities (e.g., two or three PCBs 520 for every PCB 515).

The conversion layers with photo-luminescent materials may be disposed above some or all of the LEDs, and following conversion, light from all LEDs is mixed in the waveguide as described above. For example, blue light or UV-A light may interact with phosphor material, and some of it is converted to a different color. The converted light and the remaining bluelight are mixed with the red and UV-A light, and extracted out from the waveguide plate to form white light illumination. The red light is used to tune the white light color coordinates to fit the required CCT and to improve CRI values, so it may be necessary to control the amplitude and/or duty cycle only of the red LEDs 104-1. Additional white LED at a specific CCT, may be assembled on the PCB to enable True Tunable White (TTW) functionality—i.e., the ability to tune the CCT along the black-body curve of white light from deep warm (e.g., 1800K) to far cool (e.g., 6500K) with small deviation, i.e., below 1 Macadams ellipse).

Figure 6:
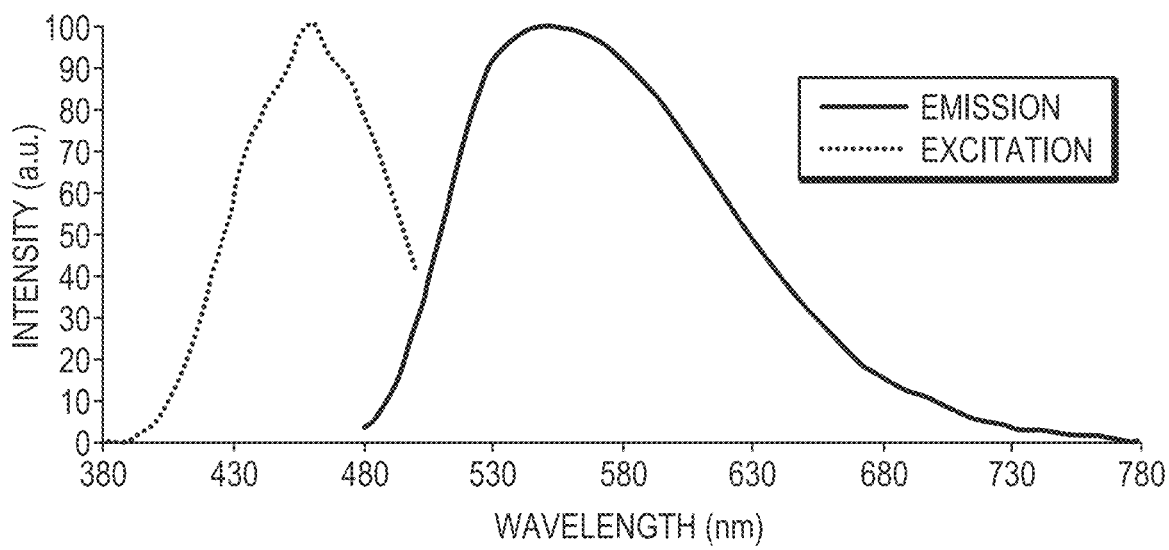
FIGS. 6 and 7 graphically depict excitation and emission spectra for photo-luminescent materials useful in connection with embodiments of the invention.
Figure 7:
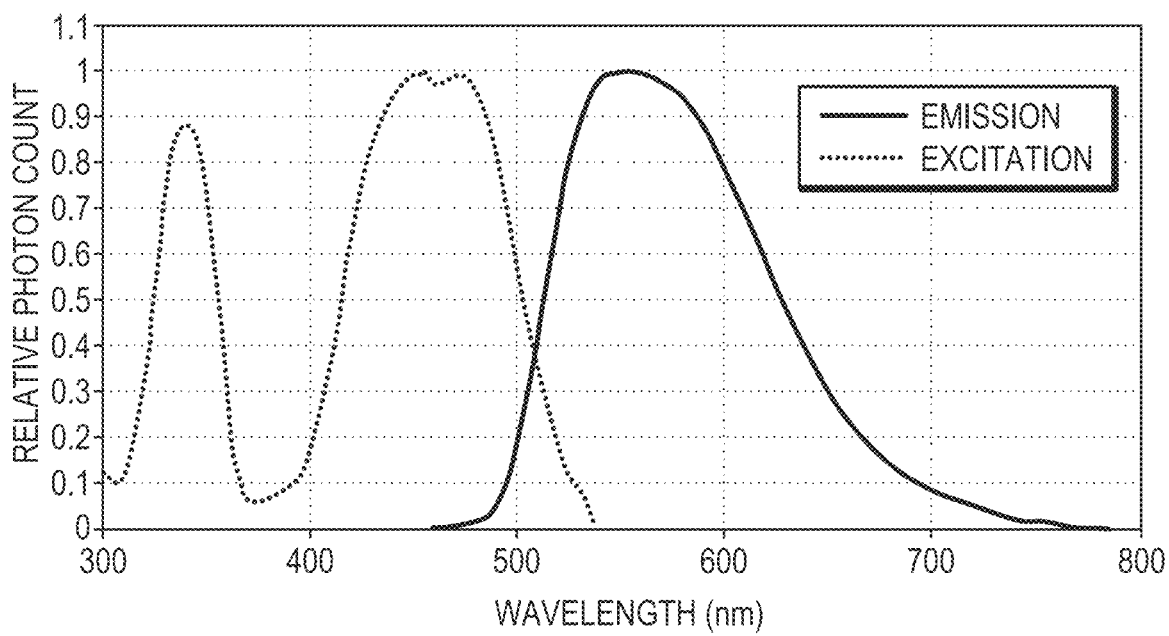

The UV-A light may interact with the photo-luminescent material and increase the amount of converted light. This will change the CCT of the light. In this case the intensity of the red light may be increased to shift the color coordinates to fit the required CCT. One option is to use a photo-luminescent material having a very low excitation level at the UV-A wavelength (e.g., Yttrium Aluminium Oxide: Cerium $Y_3Al_5O_{12}$:Ce), as shown in FIG. 6. In this case, the photo-luminescent material will convert less UV-A light to a different color. A second option is to have the phosphor excitation wavelength include the UV-A wavelength as shown in FIG. 7 (e.g., Yttrium Aluminum Garnet "537 nm"). In this case, the photo-luminescent material will convert more UV-A light to a different color. In implementations where the UV-A LEDs are connected and driven together with the blue or the red LEDs when the system is operated to provide white light, some of the UV-A light will be converted and will change in CCT. In order to maintain the target CCT, the ratio of the red and blue light may be changed. In order to retain an intense UV-A emission, it is desirable to choose a wavelength that does not interact much with the phosphor material. However, placing the UV-A LEDs in the blue channel will reduces the blue light intensity and therefore the converted light. In that case it is preferable to use UV-A LEDs that exhibit greater interaction with the phosphor material in the red channel together with the red LEDs so their light will collectively increase the amount of converted light while increasing the red:blue ratio for maintaining the target CCT.

Figure 8:
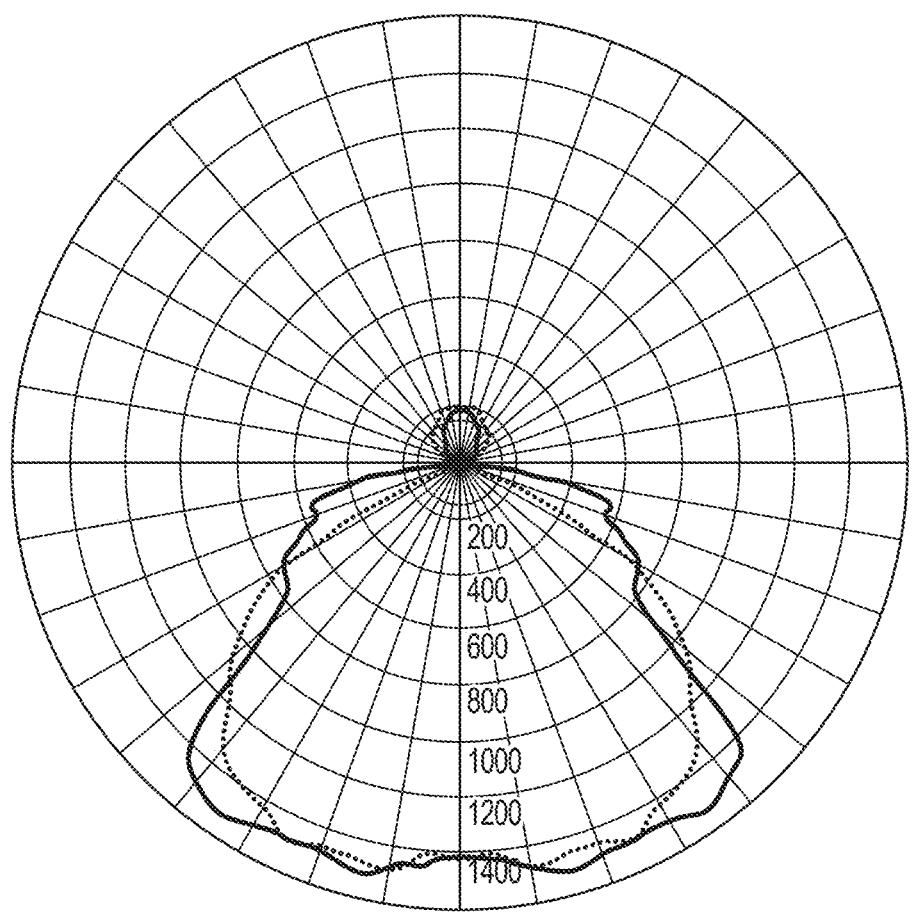
FIG. 8 depicts a representative angular UV-A light distribution from a luminaire based on an embodiment of the present invention.
Figure 9:
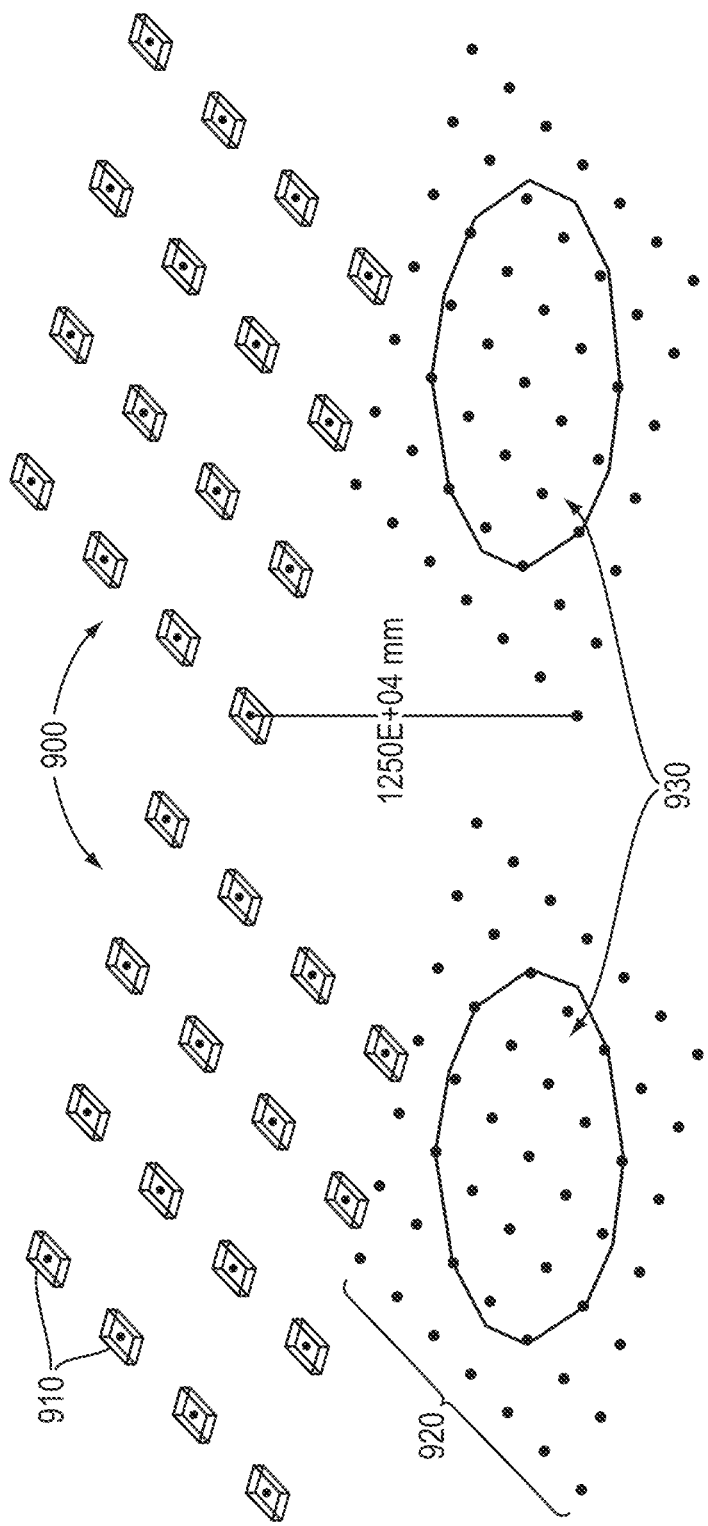
FIG. 9 illustrates the UV-A distribution over a room-size space of an array of luminaires as shown in FIG. 8.

The LED configurations 500 can be organized into a lighting fixture or "luminaire." In a "normal" mode of operation, the luminaire can provide conventional white light and germicidal UV-A light. For example, the UV-A emission may be ~7 W together with the required intensity of white light. As shown in FIG. 8, each luminaire may, in some embodiments, provide white light over a wide coverage area but UV-A light over a restricted angular range. FIG. 9 illustrates how this permits a ceiling arrangement 900 of luminaires 910 to illuminate a room-size area 920 with white light but focus UV-A energy on a smaller target area 930. In particular, the luminaires may operate in a "boost" mode in which the red and UV-A LEDs are active and operated at maximum power, and the blue LEDs are not active; for example, with reference to FIG. 5A, only output channels B and C are active. As a result, the UV-A intensity (or irradiance in w/m$^2$) in boost mode may be three times that in normal mode, and may exceed the maximum safe intensity (or irradiance) for human exposure. The red light provides a visual indication of danger. Alternatively or in addition, occupancy sensors (such as passive infrared (PIR) sensors, ultrasonic sensors, cameras, etc.) may communicate with the controller 112, which permits boost-mode operation only when no personnel are detected in the region 930 or even in the room 920.

The control circuitry 112 may include or be connected to one or more modules implemented in hardware, software, or a combination of both. For embodiments in which the functions are provided as one or more software programs, the programs may be written in any of a number of high level languages such as PYTHON, FORTRAN, PASCAL, JAVA, C, C++, C#, BASIC, various scripting languages, and/or HTML. Additionally, the software can be implemented in an assembly language directed to the microprocessor resident on a target computer; for example, the software may be implemented in Intel 80x86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. Embodiments using hardware circuitry may be implemented using, for example, one or more FPGA, CPLD or ASIC processors.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A lighting device producing white light having a target color correlated temperature (CCT) value and UV-A radiation, the device comprising:
    a plurality of red LEDs emitting red light having a wavelength between approximately 600 nm and approximately 670 nm, a plurality of blue LEDs emitting blue light having a wavelength between approximately 440 nm and approximately 485 nm, and a plurality of UV-A LEDs emitting UV radiation having a wavelength between approximately 315 nm and approximately 420;
    at least one photo-luminescent material for shifting a CCT value of at least one of (a) the red LEDs, (b) the blue LEDs or (c) the UV-A LEDs; and
    a waveguide material having (i) a mixing region for mixing the shifted and any unshifted light so as to generate white light having the target CCT value and (ii) an output region for outputting the white light.

2. The lighting device of claim 1, wherein the red LEDs have an emission peak at 630 nm.

3. The lighting device of claim 1, wherein the blue LEDs have an emission peak at 450 nm.

4. The lighting device of claim 1, wherein the UV-A LEDs have an emission peak at 395 nm.

5. The lighting device of claim 1, further comprising control circuitry for adjusting a parameter associated with at least one of the red LEDs, the blue LEDs or the UV-A LEDs so as to change the target CCT value of the generated white light.

6. The lighting device of claim 5, wherein the parameter comprises at least one of an amplitude or a duty cycle of a current or a voltage associated with the red LEDs, the blue LEDs and/or the UV-A LEDs.

7. The lighting device of claim 5, wherein the control circuitry is configured to adjust the parameter of each red LED, blue LED and UV-A LED to maintain the target CCT value while changing the intensity of the UV-A light.

8. The lighting device of claim 5, wherein the LEDs comprise a first group of the red LEDs and the UV-A LEDs electrically coupled to one another, a second group of the blue LEDs and the UV-A LEDs electrically coupled to one another, and a third group of the UV-A LEDs electrically coupled to one another, the control circuitry being configured to adjust each of the groups individually.

9. The lighting device of claim 8, wherein the UV-A LEDs in the third group emit light at a wavelength having a lower interaction with the photo-luminescent material than the wavelengths emitted by the UV-A LEDs in the first group or the UV-A LEDs in the second group.

10. The lighting device of claim 8, wherein the UV-A LEDs in the first group emit light at a wavelength having a higher interaction with the photo-luminescent material than the UV-A LEDs in the second group.

11. The lighting device of claim 1, wherein the photo-luminescent material comprises at least one of a phosphor, a quantum dot material or a fluorescent dye.

12. The lighting device of claim 1, further comprising a plurality of cup-shaped reflectors for at least partial collimation of light emitted from the LEDs, wherein each reflector has a top aperture and a bottom aperture and the bottom aperture has one of the LEDs disposed therein.

13. The lighting device of claim 12, wherein at least one of the reflectors is a parabolic reflector, the respective LED disposed therein being located at or near the focus of the parabolic reflector.

14. The lighting device of claim 12, further comprising an encapsulant material filled in a cavity space above one of the plurality of LEDs and surrounded by the respective reflector.

15. The lighting device of claim 12, wherein the reflectors comprise or consist essentially of silicone.

16. The lighting device of claim 1, further comprising a circuit board for mounting the LEDs thereon.

17. The lighting device of claim 16, further comprising a heat-dissipation structure thermally coupled to the circuit board for dissipating heat generated by the plurality of LEDs.

18. The lighting device of claim 1, further comprising at least one reflector located in the mixing region of the waveguide for promoting mixing of light.

19. The lighting device of claim 1, wherein the waveguide material comprises or consists essentially of silicone.

20. The lighting device of claim 1, wherein the waveguide material encapsulates at least one LED.

21. A lighting system comprising:
 a plurality of devices for producing white light having a target color correlated temperature (CCT) value and UV-A radiation, each of the devices comprising:
  a plurality of LEDs emitting visible light and a plurality of UV-A LEDs emitting UV radiation having a wavelength between approximately 315 nm and approximately 420;
  at least one photo-luminescent material for shifting a CCT value of at least some of the LEDs; and
  a waveguide material having (i) a mixing region for mixing the shifted and any unshifted light and (ii) an output region for outputting the light; and
 a controller configured to operate the plurality of devices in (a) a normal mode, powering the LEDs, so as to generate white light having the target CCT value while emitting UV-A light or (b) in a boost mode, powering fewer than all of the LEDs emitting visible light and powering at least a majority of the UV-A LEDs at high intensity.

22. The lighting system of claim 21, wherein in the normal mode, the UV-A light has an intensity that is safe for human exposure and in the boost boost mode the intensity exceeds the intensity that is safe for human exposure.

23. The lighting system of claim 22, wherein in the the boost mode, LEDs emitting red light are operated to indicate a risk of harmful radiation.

24. The lighting system of claim 21, wherein the plurality of LEDs emitting visible light comprise (i) a plurality of red LEDs emitting red light having a wavelength between approximately 600 nm and approximately 670 nm and (ii) a plurality of blue LEDs emitting blue light having a wavelength between approximately 440 nm and approximately 485 nm.

* * * * *